US012611103B2

(12) United States Patent (10) Patent No.: US 12,611,103 B2
Nagarajan et al. (45) Date of Patent: Apr. 28, 2026

(54) 3-DIMENSIONAL IMAGING DEVICE FOR EYE IMAGING

(71) Applicant: REMIDIO INNOVATIVE SOLUTIONS PVT. LTD, Bangalore (IN)

(72) Inventors: Shanmuganathan Nagarajan, Thiruvarur (IN); Anand Sivaraman, Bangalore (IN)

(73) Assignee: Remidio Innovative Solutions PVT.LTD, Bangalore (IN)

( * ) Notice: Subject to any disclaimer, the term of this patent is extended or adjusted under 35 U.S.C. 154(b) by 311 days.

(21) Appl. No.: 18/264,223

(22) PCT Filed: Mar. 23, 2022

(86) PCT No.: PCT/IN2022/050286
§ 371 (c)(1),
(2) Date: Aug. 3, 2023

(87) PCT Pub. No.: WO2022/201194
PCT Pub. Date: Sep. 29, 2022

(65) Prior Publication Data
US 2024/0032792 A1 Feb. 1, 2024

(30) Foreign Application Priority Data
Mar. 23, 2021 (IN) .............................. 202141012595

(51) Int. Cl.
*A61B 3/14* (2006.01)
*A61B 3/00* (2006.01)
*A61B 3/12* (2006.01)
(52) U.S. Cl.
CPC .............. *A61B 3/14* (2013.01); *A61B 3/0033* (2013.01); *A61B 3/12* (2013.01)

(58) Field of Classification Search
CPC ............ A61B 3/14; A61B 3/0033; A61B 3/12
(Continued)

(56) References Cited

U.S. PATENT DOCUMENTS 11,737,665 B2 * 8/2023 Ralston ................ A61B 3/0008
351/206
2015/0009473 A1 * 1/2015 Su ........................ A61B 3/1208
351/206
(Continued)

FOREIGN PATENT DOCUMENTS

JP 2015177403 A 10/2015
JP 2020174862 A 10/2020

OTHER PUBLICATIONS

Notice of Reasons for Refusal, dated Dec. 10, 2025, for corresponding Japanese Patent Application No. 2023-549926, 11 pages. (with English Translation).

*Primary Examiner* — Mohammed A Hasan
(74) *Attorney, Agent, or Firm* — Seed Intellectual Property Law Group LLP

(57) ABSTRACT

The present subject matter relates to a 3-dimensional (3D) imaging device (100) for imaging various structures of eye. The 3D imaging device (100) comprises a 3D viewing unit (102) detachably coupled to an eye imaging unit (104). An imaging module (103) may be placed in between the 3D viewing unit (102) and the eye imaging unit (104) for capturing images or videos of eye The eye imaging unit 104 comprises an imaging lens (106), an illumination module (108), a machine learning module (110), a control module (112), a processor (114), and a memory (116). The components of the eye imaging unit (104) are arranged in such a way that they are used for both slit lamp imaging and ophthalmic imaging of the eye.

14 Claims, 12 Drawing Sheets

(58) Field of Classification Search
　　USPC ......................................................... 351/206
　　See application file for complete search history.

(56)　　　　　　　　References Cited

U.S. PATENT DOCUMENTS

| | | | |
|---|---|---|---|
| 2015/0256817 A1 | 9/2015 | Hofeldt | |
| 2016/0249806 A1* | 9/2016 | Yates | A61B 3/12 |
| | | | 351/207 |
| 2016/0270656 A1* | 9/2016 | Samec | A61B 5/398 |
| 2019/0117064 A1* | 4/2019 | Fletcher | A61B 3/145 |
| 2020/0405147 A1* | 12/2020 | Nagarajan | A61B 3/158 |
| 2021/0072890 A1* | 3/2021 | Agarwal | G06F 3/0488 |

* cited by examiner

3-DIMENSIONAL IMAGING DEVICE FOR EYE IMAGING

TECHNICAL FIELD

The present subject matter relates generally to an imaging device for eye imaging, and in particular to a 3-dimensional imaging device for imaging various structures of eye.

BACKGROUND

Current ophthalmic instruments such as ophthalmoscopes and slit lamps allow an ophthalmologist to see different structures of the eye to screen for eye diseases. The slit lamp is an ophthalmic instrument with a moveable slit light source and a binocular microscope with which the ophthalmologist can examine the anterior segment of the eye. When combined with different lenses, the slit lamp can also be used for examination of the posterior segment of the eye. Ophthalmoscope, for example, an indirect ophthalmoscope is an ophthalmic instrument that allows the ophthalmologist to gain a view of the cornea, retina or other portion of the eye. In indirect ophthalmoscope, a light source from the indirect ophthalmoscope is directed into the patient's eye and the reflected light is gathered by a condensing lens to form an image of the patient's eye under observation. The obtained image can be viewed by the ophthalmologist through a view finder and/or through display units.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components where possible.

DETAILED DESCRIPTION

Figure 1:
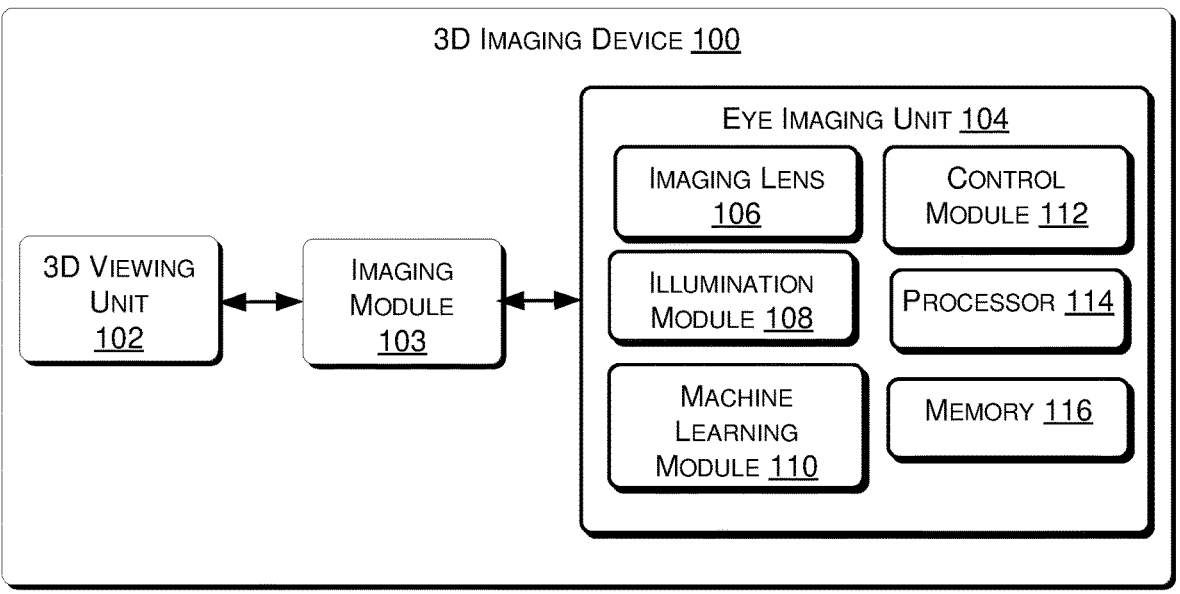
FIG. 1 illustrates a block diagram of a 3-dimensional imaging device, in accordance with an embodiment of the present subject matter.

The present subject matter relates generally to an imaging device for eye imaging, and in particular to a 3-dimensional imaging device for imaging various structures of the eye.

Currently, various ophthalmic instruments are used by ophthalmologists for examining and imaging the posterior and anterior structures of the eye. For example, a binocular indirect ophthalmoscope has become an indispensable tool to diagnose and manage a variety of vitreoretinal disorders including lattice degeneration, retinal holes or tears, retinal detachment, retinopathy of prematurity, retinoschisis, sickle cell retinopathy, and an array of other diseases. Modern indirect ophthalmoscopes are developed with a myriad of features, which may include adjustable inter pupillary distance, portable power packs, adjustable mirrors, dust sealed optics, and red free and cobalt blue filters. Video capture capabilities built in some indirect ophthalmoscopes allow the patient to see his or her fundus on a video and students also greatly benefit from this feature.

Typical indirect ophthalmoscopes can only provide wider field of view of about 0.5× to 0.8× magnification. Also, there is no mechanism in traditional ophthalmoscopes to switch between magnified field of view and normal field of view of the eye. Additionally, color filters are required in the indirect ophthalmoscope for viewing various structures of the eye, for example, a red-free filter can be used to view blood, membranes, new vessels, retinal nerve fiber layer defects, and highlights whitish portions of the retina. Further, for performing examination using the slit lamps or ophthalmoscopes, the patient's eye needs to be dilated for allowing a better view of the posterior section of the eye, which may be uncomfortable for the patient. Therefore, there is a need for a device which can overcome the above problems and other disadvantages of traditional ophthalmic instruments.

The present subject matter discloses a 3-dimensional (3D) imaging device for imaging various structures of the eye. In an aspect of the present subject matter, the 3D imaging device comprises a 3D viewing unit and an eye imaging unit. In an example, the 3D viewing unit is detachably coupled to the eye imaging unit. The 3D viewing unit can be a Virtual reality (VR) box or a smart glass. In an example, when the VR box is used as the 3D viewing unit, a smartphone may be placed in between the 3D viewing unit and the eye imaging unit for converting the 2D images or video into immersive 3D images or video.

The eye imaging unit comprises an imaging lens, an illumination module, a machine learning module, a control module, a processor, and a memory. The imaging lens may be used for magnifying and viewing various structures of the eye. In an example, the imaging lens allows for high magnification of the eye of about 2× to 4× magnification. Further, the magnification can also be switched between standard view of about 0.5× to 0.8× to magnified view of about 2× to 4×. The illumination module comprises one or more light sources such as light emitting diodes LED's for illuminating the eye. In an example, infrared light may be used to view a video or images of the eye. This invisible infrared light source allows viewing structures of the eye without dilating the eye and a visible light may be used for capturing the images of the eye. In addition, a multicolor LED with wavelength and functionality of typical color filters may be used for viewing different structures of the eye.

The eye imaging unit may be used for both slit lamp imaging and ophthalmic imaging. When the eye imaging unit is used for slit lamp imaging, the illumination module may move by 45 degrees on both the sides of the imaging axis of the imaging lens. On the other hand, when the eye imaging unit is used for ophthalmic imaging, the imaging lens and the illumination module may be moved to a position off the imaging axis of the imaging lens. Further, the control module of the eye imaging unit may be used to control the imaging lens and the illumination module.

In an aspect of present subject matter, the eye imaging unit provides 2-dimensional (2D) images of the eye. The eye imaging unit is connected to the 3D viewing unit, such as VR box or smart glass, where the 3D viewing unit converts the 2D images or 2D videos into 3D images or 3D videos. When the VR box is used as 3D viewing unit, an imaging module, such as a smartphone, may be placed in between the 3D viewing unit and the eye imaging unit. In an example, an application installed on the smartphone may be used for converting the 2D images or 2D videos into 3D image or 3D videos.

Further, the machine learning module of the eye imaging unit may be used for automatic capture of 3D images. In an example, the machine learning module may automatically convert the captured infrared images into color images and displaying on the 3D viewing unit. In an example, the machine learning module may further allow an ophthalmologist to provide gestures or finger movements to control the operations of the VR box or smart glass. Further, the machine learning module may also be used for controlling the application installed on the smartphone using voice commands.

Thus, the 3-dimensional imaging device of the present subject matter allows an ophthalmologist to view images or videos of various structures of the eye in 3-dimensions and to automatically capture the 3D images in real time. The 3D imaging device can also be used for both slit lamp imaging and ophthalmic imaging. Further, the 3D imaging device provides a greater magnification of the eye of about 2× to 4× and the magnification level can be switched between magnified field of view and standard field of view. Since, infrared light source is used for illuminating the eye for viewing, dilation of eye before the examination can be eliminated. Further, usage of traditional color filters may also be avoided, as the multicolor LED with same wavelength and same functionality as that of the traditional color filters are used for viewing various structures of the eye. The 3-dimensional imaging device can also be used for indirect/direct ophthalmoscope imaging/video, Gonioscope imaging, laser surgery imaging, Retinopathy of prematurity imaging, Anterior segment imaging, Narrow and wide-angle imaging, fundus fluorescein angiography, etc.

Aspects of the present subject matter are further described in conjunction with the appended figures. It should be noted that the description and figures merely illustrate the principles of the present subject matter. It will thus be appreciated that various arrangements that embody the principles of the present subject matter, although not explicitly described or shown herein, can be devised from the description and are included within its scope. Moreover, all statements herein reciting principles, aspects, and implementations of the present subject matter, as well as specific examples thereof, are intended to encompass equivalents thereof.

FIG. 1 illustrates a block diagram of a 3-dimensional imaging device, in accordance with an embodiment of the present subject matter. The 3-dimensional (3D) imaging device 100 comprises a 3D viewing unit 102 and an eye imaging unit 104. The 3D viewing unit 102 may be detachably coupled to the eye imaging unit 104. Examples of the 3D viewing unit 102 may include, but are not limited to, a Virtual reality (VR) box or a smart glass. In an example, if the VR box is used as the 3D viewing unit 102, an imaging module 103, such as a smartphone, may be placed in between the 3D viewing unit 102 and the eye imaging unit 104 for converting 2D images or 2D videos to immersive 3D images or 3D videos.

The eye imaging unit 104 comprises an imaging lens 106, an illumination module 108, a machine learning module 110, a control module 112, a processor 114, and a memory 116. The processor 114 may be implemented as microprocessors, microcomputers, microcontrollers, digital signal processors, central processing units, state machines, logic circuitries, and/or any devices that manipulate signals based on operational instructions. Among other capabilities, the processor 114 may fetch and execute computer-readable instructions. The functions of the processor 114 may be provided through the use of dedicated hardware as well as hardware capable of executing machine readable instructions.

The eye imaging unit 104 may also include the memory 116 coupled to the processor 114. The memory 116 may include any non-transitory computer-readable medium including volatile memory (e.g., RAM), and/or non-volatile memory (e.g., EPROM, flash memory, Memristor, etc.). The memory 116 may also be an external memory unit, such as a flash drive, a compact disk drive, an external hard disk drive, a database, or the like.

The eye imaging unit 104 may be used with a variety of devices, such as slit lamp imaging and ophthalmic imaging. In an example implementation, when the eye imaging unit 104 is used for slit lamp imaging, the illumination module 108 may move by 45 degrees on both the sides of the imaging axis of the imaging lens 106. In another example, when the eye imaging unit 104 is used for ophthalmic imaging, the illumination module 108 may be moved to a position off the imaging axis of the imaging lens 106. The illumination module 108 may be moved to different positions within the imaging device either manually, i.e., by utilizing various knobs included in the imaging device, or automatically, i.e., based on instructions received from the control module 112. In either situation, to allow the movement of the illumination module 108 within the imaging device, the illumination module 108 may be placed on a set of guide rails (not shown) arranged within the imaging module. In an example, a guide rail from the set of guide rails may be arranged to allow the illumination module 108 to be moved by 45 degrees on both the sides of the imaging axis of the imaging lens. In the example, another guide rail from the set of guide rails may be arranged to allow the illumination module 108 to be moved to a position off the imaging axis of the imaging lens.

In an example, when the illumination module 108 is moved to different positions within the imaging device automatically, a set of motors (not shown) included in the imaging device may be used to control the movement of the illumination module 108 within the imaging device. In the example, the operation of the motors may be controlled by the control module 112 to control the movement of the illumination module 108 within the imaging device.

In an example, when the VR box is used as the 3D viewing unit 102, the imaging lens 106 may be used for magnifying and viewing various structures of the eye. In the example, the imaging lens 106 may be placed in front of a built-in camera of the imaging module 103, such as the smartphone, where the imaging module 103 may be placed between the eye imaging unit 104 and the VR box. Further, in the example, the smartphone may have an application installed thereon, where the application converts the captured 2D images or 2D videos to 3D images or videos which is displayed on the displays of the VR box.

In another example, when the smart glass is used as the 3D viewing unit 102, the imaging module 103, such as a camera, may be mounted to the smart glass. In the example, the imaging lens 106 may be placed in front of the camera of the smart glass for the ophthalmic imaging as well as the slit lamp imaging. Further, in the example, the processor 114 of the eye imaging unit 104 may convert the 2D images or videos captured by the imaging module 103 into 3D images or videos. The 3D images and videos may then be displayed on the displays of the smart glass.

In an example, the 3-dimensional imaging device 100 can be used for indirect/direct ophthalmoscope imaging/video, Gonioscope imaging, laser surgery imaging, Retinopathy of prematurity imaging, Anterior segment imaging, Narrow and wide-angle imaging, and fundus fluorescein angiography. In an example, when the 3-dimensional imaging device is used for gonioscope imaging, a gonio lens may be placed between smart glass or VR box and the eye. Thus, the 3-dimensional imaging device of the present subject matter allows an ophthalmologist to view images or videos of the eye for various applications in 3-dimensions and to automatically capture the 3D images in real time.

Figure 2A:
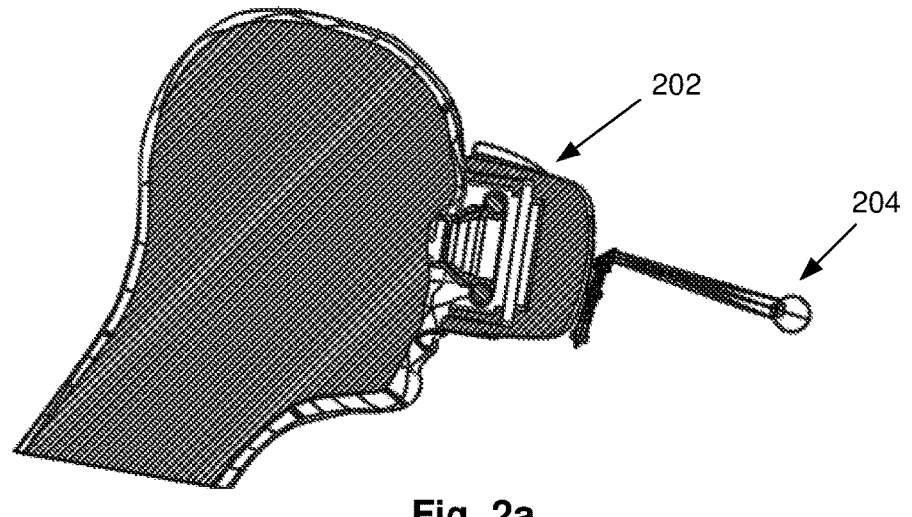
FIG. 2a illustrates an example VR box as a 3D viewing unit for slit lamp imaging, in accordance with an embodiment of the present subject matter.

FIG. 2*a* illustrates a 3D viewing unit for slit lamp imaging, in accordance with an embodiment of the present subject matter. In an example, the 3D viewing unit may be a virtual reality (VR) box. As shown in the figure, the VR box 202 may be worn by an ophthalmologist for examination of patient's eye 204. The VR box 202 may be coupled to the eye imaging unit 104 for slit lamp imaging. As has been discussed above, the eye imaging unit 104 comprises the imaging lens 106 and the illumination module 108. For slit lamp imaging, the illumination module 108 may move by 45 degrees on both the sides of the imaging axis of the imaging lens 106. Further, as already described, the imaging lens 106 may be used for magnifying or viewing various structures of the eye. Further, the application installed in the imaging module 103, such as the smartphone, may allow the captured 2D images or 2D videos to be converted into 3D images or 3D videos which may be displayed on a display of the VR box 202.

Figure 2B:
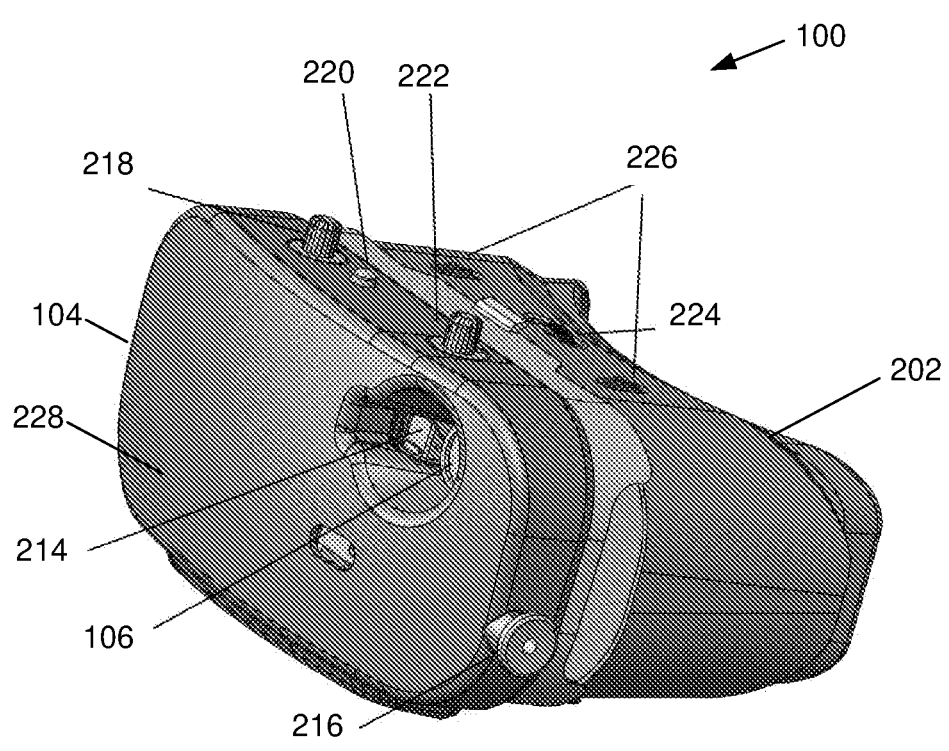
FIG. 2b illustrates an isometric view of example 3D imaging device for slit lamp imaging, where the eye imaging unit is coupled to the VR box, in accordance with an embodiment of the present subject matter.

FIG. 2*b* illustrates an isometric view of the 3D imaging device 100 for slit lamp imaging, where the eye imaging unit 104 is coupled to the VR box 202, in accordance with an example of the present subject matter. As has been discussed, the eye imaging unit 104 comprises the imaging lens 106 and the illumination module 108. For slit lamp imaging using the VR box 202, the illumination module 108 may move by 45 degrees on both the sides of the imaging axis of the imaging lens 106. Further, as already described, the imaging lens 106 may be placed in front of a camera (not shown in the FIG. 2*b*) of imaging module 103 for capturing images or videos of the eye.

In an example, the illumination module 108 may include an illumination assembly 214 including one or more infrared light sources, such as infrared light emitting diodes (LED) for illuminating the eye. The infrared light source may allow viewing of images of the eye without dilating the eye of the patient. In the example, the illumination assembly 214 may further include a multicolor LED.

The illumination module 108 may further include an illumination circle diameter changing knob 216 to change a size of an illumination circle being formed by the infrared LED. In an example, the standard output of the illuminated circle diameter may be one of 50 mm, 37 mm, and 17 mm.

Further, the eye imaging unit 104 may include a light intensity control knob 218 for controlling the intensity of light emitted by the multicolor LEDs and other light sources, such as the infrared LED present in the illumination assembly 214. The eye imaging unit 104 may further include a multicolor LED switching control 220 for switching between different colors of the multicolor LED. The multicolor LED (not shown in FIG. 2*b*) may have wavelength and functionality as that of traditional color filters that are used for viewing various structures of the eye. In an example, the eye imaging unit 104 may also include an LED angle changing knob 222 for changing the angle of illumination assembly by 45 degrees on both the sides of the imaging axis of the imaging lens.

In an example implementation, the imaging module 103 may capture the 2D images or 2D videos of the patient's eye. In an example, the imaging lens 106 may be placed in front of a built-in camera of the imaging module 103, such as the smartphone, which is placed between the eye imaging unit 104 and the VR box. In an example, the smartphone is embedded with an application which converts the captured 2D images or 2D videos to 3D images or 3D videos which is displayed on the displays of the VR box.

The VR box 202 also comprises an interpupillary changing knob 224 for adjusting the displays of the VR box corresponding to the interpupillary distance of the both the eyes of the ophthalmologist. Further, the VR box also includes a pair of eye power changing knobs 226. In an example, eye power changing knobs are used to change the focus of the display based on the refraction power of the eyes of the ophthalmologist who is viewing the display. The eye imaging unit 104 comprising all the components are secured by a cover 228 as shown in the FIG. 2*b*.

Figure 2C:
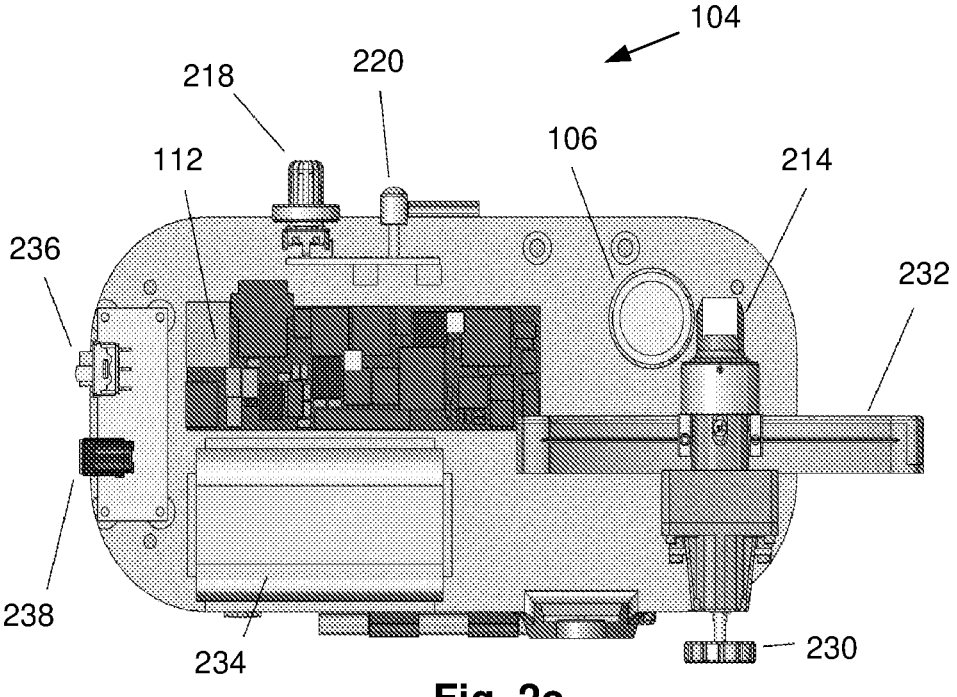
FIG. 2c illustrates front view of an eye imaging unit for slit lamp imaging, in accordance with an embodiment of the present subject matter.

FIG. 2c illustrates front view of an eye imaging unit 104 for slit lamp imaging, in accordance with an example of the present subject matter. The imaging lens 106 is used for magnifying and viewing various structures of the eye. In an example, illumination module 108 may vary between +45 to −45 degrees and moves at both the sides of the imaging axis of the imaging lens 106. As shown in the FIG. 2c, a slit width changing knob 230 is used for changing the width between zero to 12 mm, so that the ophthalmologist can stop at any position of the slit width between zero to 12 mm. Further, illumination assembly 214 is provided on a slit angle changing assembly 232 for changing the angle of illumination assembly 214 at 45 degrees on both the sides of the imaging axis of the imaging lens 106.

Figure 2D:
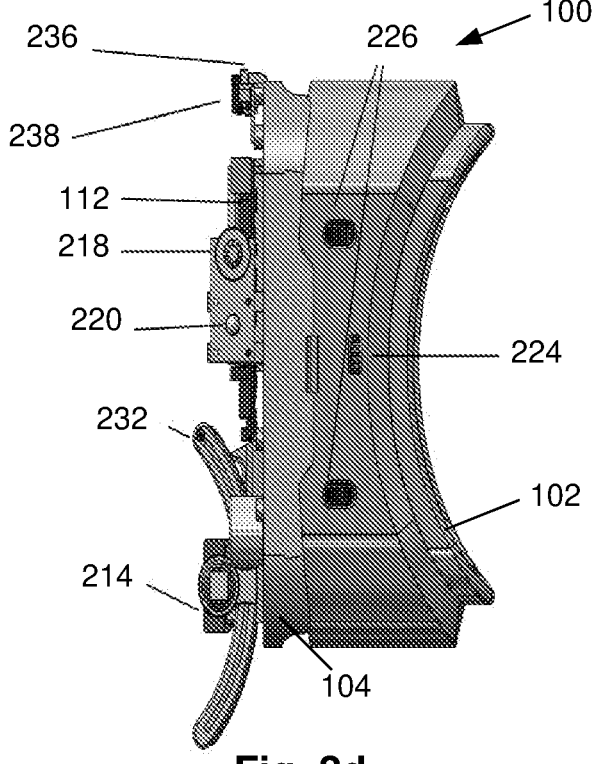
FIG. 2d illustrates side view of an example 3D imaging device for slit lamp imaging, in accordance with an embodiment of the present subject matter.

The eye imaging unit 104 also includes the control module 112 to control operations of various components of the eye imaging unit such as the imaging lens, illumination module, etc. Further, the eye imaging unit 104 also comprises a battery 234 for supplying power to the multicolor LED and the illumination assembly 214. Additionally, the eye imaging unit 104 includes an on/off switch 236 and a power input 238. In an example, the eye imaging unit 104 can be switched off using the switch 236 while not in use. FIG. 2d illustrates side view of an example 3D imaging device for slit lamp imaging, in accordance with an embodiment of the present subject matter.

Figure 2E:
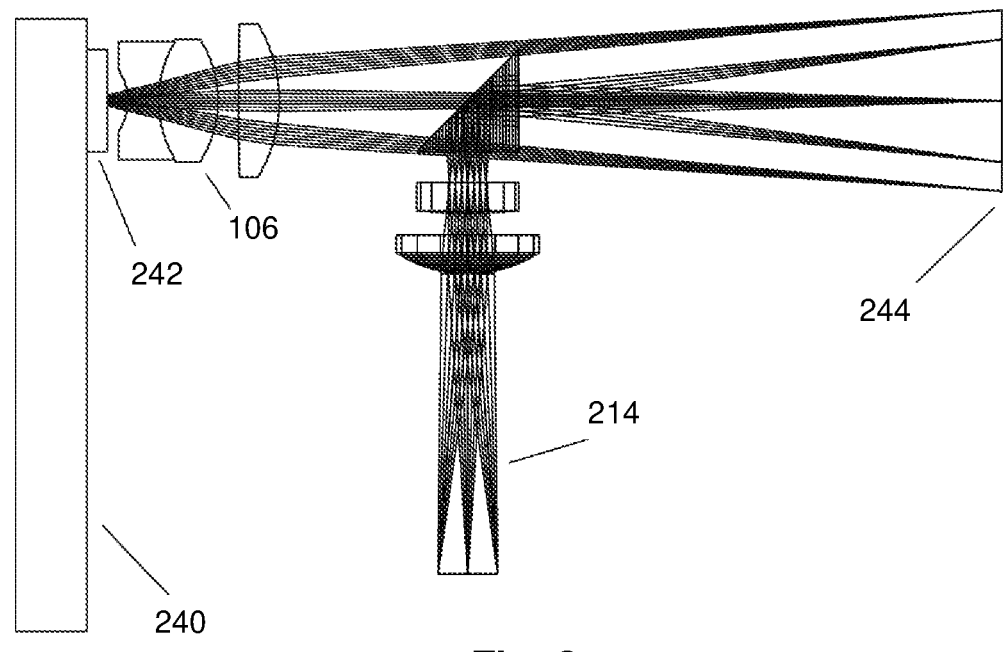
FIG. 2e illustrates optical layout of slit lamp imaging using an example smartphone, in accordance with an embodiment of the present subject matter.

FIG. 2e illustrates an optical layout of slit lamp imaging using an example smartphone 240, in accordance with an embodiment of the present subject matter. The imaging lens 106 may be placed in front of a camera 242 of the smartphone 240 for examining or imaging the eye. During operation, the light from the illumination assembly 214 is projected on the patient's eye through a mirror. Further, the camera 242 of the smartphone 240 can be used to capture the image or videos of the eye. In an example, imaging lens 106 and other ocular lenses may be placed in front of camera 242 of the smartphone 240 for magnification of the captured image which can be displayed on a display of the smartphone 240.

Figure 3A:
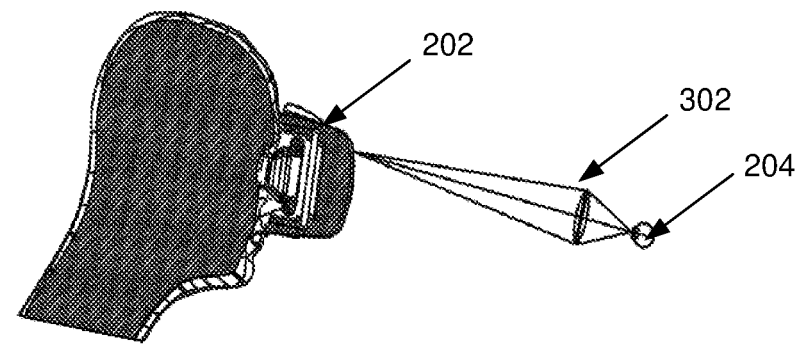
FIG. 3a illustrates an example VR box as a 3D viewing unit for ophthalmic imaging, in accordance with an embodiment of the present subject matter.

FIG. 3a illustrates an example VR box as a 3D viewing unit for ophthalmic imaging, in accordance with an embodiment of the present subject matter. As shown in the FIG. 3a, the VR box 202 is worn by an ophthalmologist for examination and imaging of the patient's eye 204. The VR box 202 is coupled to the eye imaging unit 104 for ophthalmic imaging. In an example, a condensing lens 302 may be placed in between the eye 204 of the patient and the VR box 202. In an example, for ophthalmic imaging, the imaging lens and the illumination module are at off axis. In an example, the imaging lens may be placed in front of a built-in camera of the imaging module, such as the smartphone which is placed between the eye imaging unit and the VR box. The light from the illumination module is directed to the eye 204 of the patient and the reflected light is gathered by a condensing lens 302 to form an image of the patient's eye on the display of the smartphone. In one example, the smartphone is embedded with a software which converts the captured 2D images or videos to 3D images or videos which is displayed on the two displays of the VR box.

In an example, the VR box 202 may further include one or more gesture recognition sensors (not shown). The gesture recognition sensors may detect one or more gestures and may accordingly control operation of the imaging device. In an example, the gesture recognition sensor may be coupled to the machine learning module 110, where the machine learning module 110 may utilize a machine learning model to detect the gestures and identify a corresponding operation to be performed on the imaging device. In the example, the machine learning model may be trained based on multiple gestures and operations corresponding to each of the multiple gestures.

In another example, the VR box 202 may also include other sensors, such as a microphone, to receive audio commands. In the example, the other sensors may be coupled to the machine learning module where the machine learning module may utilize a machine learning model to detect the audio commands and identify a corresponding operation to be performed on the imaging device. In the example, the machine learning model may be trained based on multiple audio commands and operations corresponding to each of the multiple audio commands.

Figure 3B:
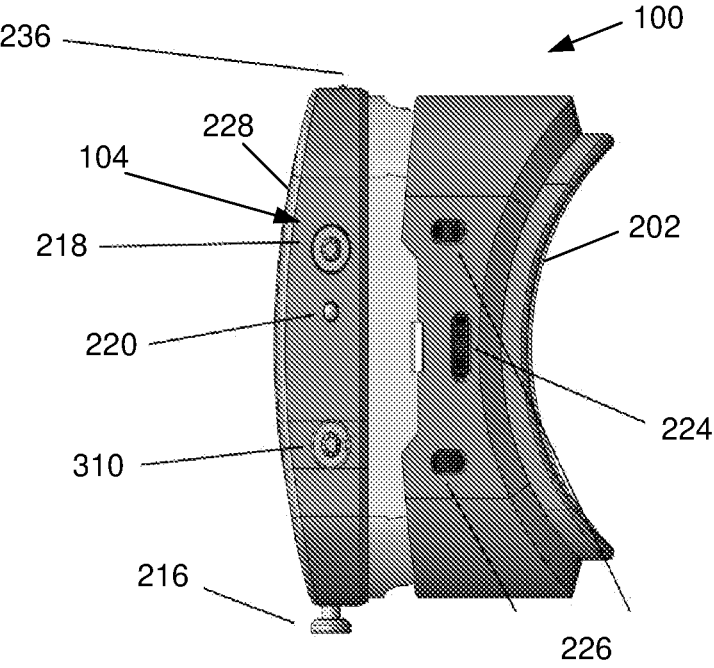
FIG. 3b illustrates top view of an example 3D imaging device for ophthalmic imaging, where the eye imaging unit is coupled to the VR box, in accordance with an embodiment of the present subject matter.

FIG. 3b illustrates top view of an example 3D imaging device 100 for ophthalmic imaging, where the eye imaging unit 104 is coupled to the VR box 202, in accordance with an embodiment of the present subject matter. For ophthalmic imaging, an imaging module such as the smartphone may be placed in between the eye imaging unit 104 and the VR box 202. As has been discussed, the eye imaging unit 104 comprises the imaging lens 106 and the illumination module 108. The imaging lens 106 may be placed in front of a built-in camera of the smartphone for magnifying and viewing the structures of the eye. Further, the illumination module is at off axis to the imaging lens for illuminating the eye. In an example, the smartphone is embedded with an application which converts the captured 2D images or 2D videos to 3D images or 3D videos which is displayed on the two displays of the VR box.

The illumination module 108 of the eye imaging unit 104 comprises a LED light angle changing knob 310 for changing the angle of LED light projected on the eye of the patient. In an example, the illumination module comprises one or more light sources, such as light emitting diodes (LED) for illuminating the eye. In an example, infrared light may be used for viewing video or images of the eye. This invisible infrared light source allows viewing of structures of the eye without dilating the eye. The eye imaging unit 104 also includes other components such as the illumination circle diameter changing knob 216 to change a size of an illumination circle being formed by the infrared LED. In an example, the standard output of the illuminated circle diameter may be one of 50 mm, 37 mm, and 17 mm. The eye imaging unit 104 may further include the light intensity control knob 218 for controlling the intensity of multicolored LEDs and other light sources, such as the infrared LED present in the illumination assembly.

The eye imaging unit 104 comprises the multicolor LED switching control 220 for switching between different colors of the multicolor LED. The multicolor LED (not shown in fig) includes wavelength and functionality same as that of the traditional color filters that are used for viewing various structures of the eye. The eye imaging unit 104 also includes the on/off switch 236 as shown in the FIG. 3b. The VR box 202 comprises the interpupillary changing knob 224 for adjusting the displays of the VR box corresponding to the interpupillary distance of the both the eyes of the ophthalmologist. Further, the VR box may also include the eye power changing knobs 226. In an example, eye power changing knobs may be used to change the focus of the display based on the refraction power of eyes of the ophthalmologist viewing the display. The eye imaging unit 104 comprising all the components are secured by the cover 228 as shown in the FIG. 3b.

Figure 3C:
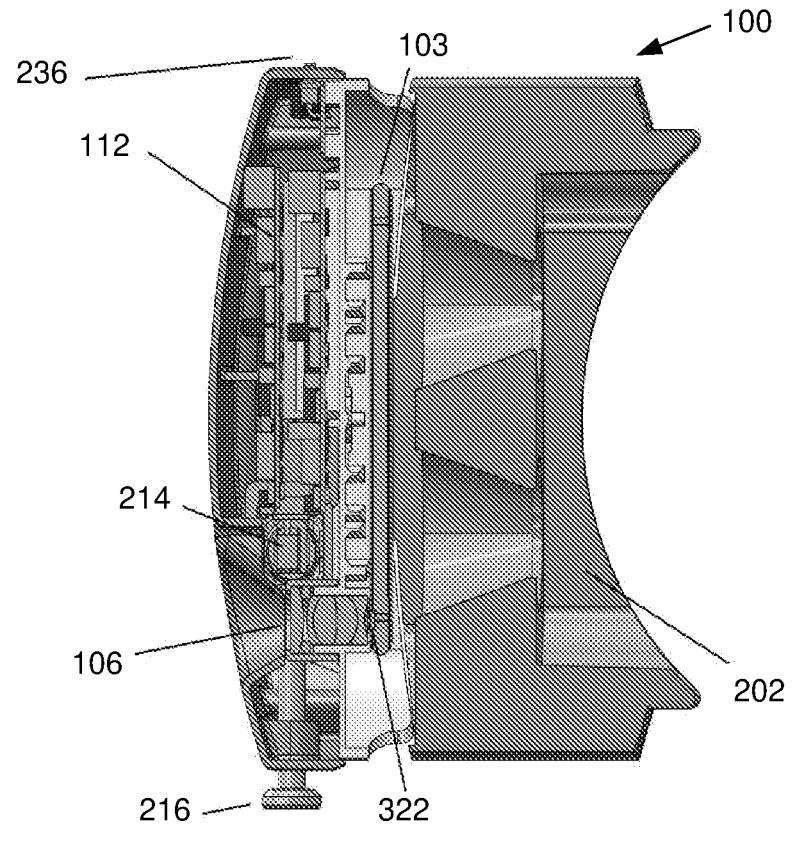
FIG. 3c illustrates top view cross section of an example 3D imaging device for ophthalmic imaging, in accordance with an embodiment of the present subject matter.

FIG. 3c illustrates top view cross section of an example 3D imaging device 100 for ophthalmic imaging, in accordance with an embodiment of the present subject matter. In an example, as shown in the figure, the imaging module 103, such as a smartphone may be placed between the VR box 202 and the eye imaging unit 104. A built-in camera 322 of the smartphone may be used for capturing the images of the eye. In an example, when utilized with the built-in camera of the smartphone, the one or more imaging lens 106 may be used for magnification of eye of about 0.5× to 0.8×. In the example, the magnification of to 0.8× may be achieved by utilizing the digital zoom of the camera of the smartphone. Further, the magnification may be switched to either 2× and/or 4× by changing a combination of the one or more imaging lenses 106 being utilized with the camera of the smartphone. The magnification of 2× and/or 4× may also be achieved by changing the combination of the one or more imaging lenses 106 along with utilization of the digital zoom of the camera of the smartphone.

In another example, the camera of the smartphone may be equipped with a single-lens reflex (SLR) lens for capturing images of the structure of the eye. In the example, a magnification of 2× to 4× may be achieved by adjusting the SLR lens included in the camera of the smartphone.

Further, the smartphone may embedded with an application which converts the captured 2D images or 2D videos to 3D images or 3D videos which is displayed on the two displays of the VR box.

Figure 3D:
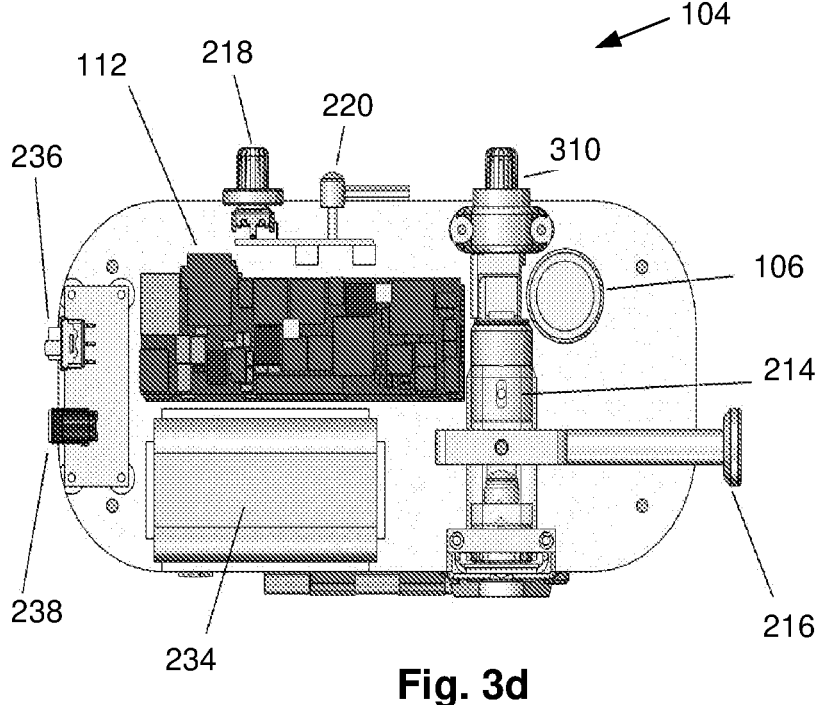
FIG. 3d illustrates a front view of an eye imaging unit for ophthalmic imaging, in accordance with an embodiment of the present subject matter.

FIG. 3d illustrates a front view of an eye imaging unit 104 for ophthalmic imaging, in accordance with an embodiment of the present subject matter. As has been explained, the imaging lens 106 may be used for magnifying and viewing the structures of eye and the illumination assembly 214 is used for illuminating the eye. The eye imaging unit 104 may comprise the light intensity control knob 218 for controlling the intensity of multicolored LEDs and other light sources, such as the infrared LED present in the illumination assembly. The eye imaging unit 104 comprises the multicolor LED switching control 220 for switching between the different colors of the multicolor LED. The multicolor LED (not shown in fig) includes wavelength and functionality same as that of the traditional color filters that are used for viewing various structures of the eye. In an example, the different colors of the multicolor LED may be switched to view and capture different structures of the eye. For instance, when images and/or videos of nerves present within retina of the eye are to be captured, the multicolor LED switching control 220 may switch the multicolor LED to emit red light. It would be noted that to capture the images and/or videos of the structures of the eye, the infrared LED and the multicolor LED may be illuminated simultaneously.

The eye imaging unit 104 also comprises the LED light angle changing knob 310 for changing the angle of LED light projected on the eye of the patient. Further, the eye imaging unit 104 also comprises the battery 234 for suppling power to the multicolor LED and the illumination assembly 214. Additionally, the eye imaging unit 104 includes the on/off switch 236 and the power input 238 as shown in FIG. 3d. In an example, the eye imaging unit 104 can be switched off using the switch 236 while not in use.

Figure 3E:
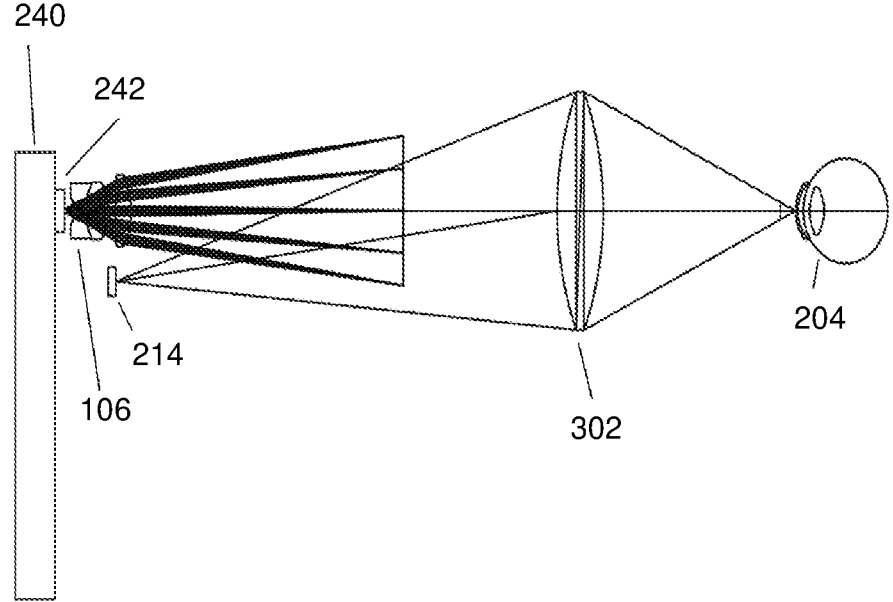
FIG. 3e illustrates an optical layout of ophthalmic imaging using an example smartphone, in accordance with an embodiment of the present subject matter.

FIG. 3e illustrates an optical layout of ophthalmic imaging using an example smartphone, in accordance with an embodiment of the present subject matter. The imaging lens 106 may be placed in front of the camera 242 of the smartphone 240 for examining or imaging the eye 204. The illumination assembly 214 with LED light source is at off axis to the imaging lens for ophthalmic imaging. During operation, the light from the illumination assembly 214 is projected on the patient's eye 204. The reflected light from the eye 204 is gathered by a condensing lens 302 to form an image of the patient's eye under observation.

Figure 4A:
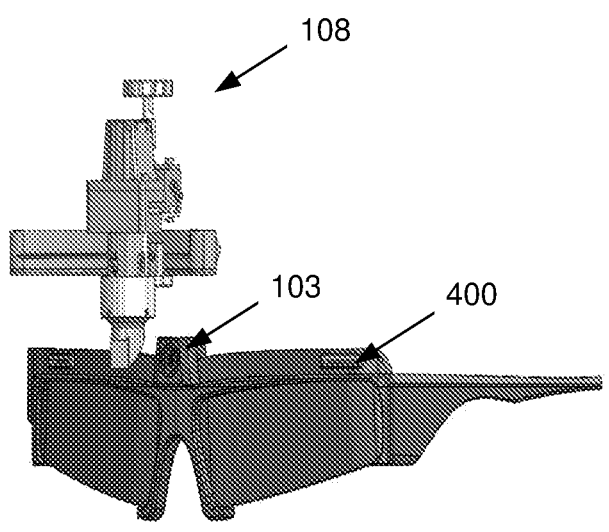
FIG. 4a illustrates an example smart glass as a 3D viewing unit for slit lamp imaging and ophthalmic imaging, in accordance with an embodiment of the present subject matter.

FIG. 4a illustrates an example smart glass 400 as a 3D viewing unit for slit lamp imaging and ophthalmic imaging, in accordance with an embodiment of the present subject matter. In an example, when the smart glass 400 is used for ophthalmic imaging, then the 3D viewing unit may be locked at a particular position. In an example, the smart glass 400 may be worn by an ophthalmologist for examination and imaging of patient's eye. The illumination module 108 is coupled to the smart glass 400 as shown in the figure. In an example, the imaging module 103, such as a camera, may be attached to the smart glass 400. The camera is used for capturing the images or videos of the eye of the patient.

In an example, the illumination module 108 includes a light source for projecting the light on the eye. The reflected image is then captured using the camera of the smart glass 400. In an example, the reflected 2D image is split into two screens with a bit of path difference thus, a 3D image will be displayed on the displays of smart glass 400. In an example, the processor 114 of the eye imaging unit 104 may be used for converting 2D images or 2D videos to 3D images or 3D videos. In an example, the illumination module 108 comprises one or more light sources such as light emitting diodes LED's for illuminating the eye. In an example, infrared light may be used to view the video or images of the eye. This invisible infrared light source allows viewing of images of eye without dilating the eye.

In an example, the smart glass 400 may further include one or more gesture recognition sensors (not shown). The gesture recognition sensors may identify one or more gestures and may accordingly control operation of the imaging device. In an example, the gesture recognition sensor may be coupled to the machine learning module 110, where the machine learning module 110 may utilize a machine learning model to detect the gestures and identify a corresponding operation to be performed on the imaging device. In the example, the machine learning model may be trained based on multiple gestures and operations corresponding to each of the multiple gestures.

In another example, the smart glass 400 may also include other sensors, such as a microphone, to receive audio commands. In the example, the other sensors may be coupled to the machine learning module where the machine learning module may utilize a machine learning model to detect the audio commands and identify a corresponding operation to be performed on the imaging device. In the example, the machine learning model may be trained based on multiple audio commands and operations corresponding to each of the multiple audio commands.

Figure 4B:
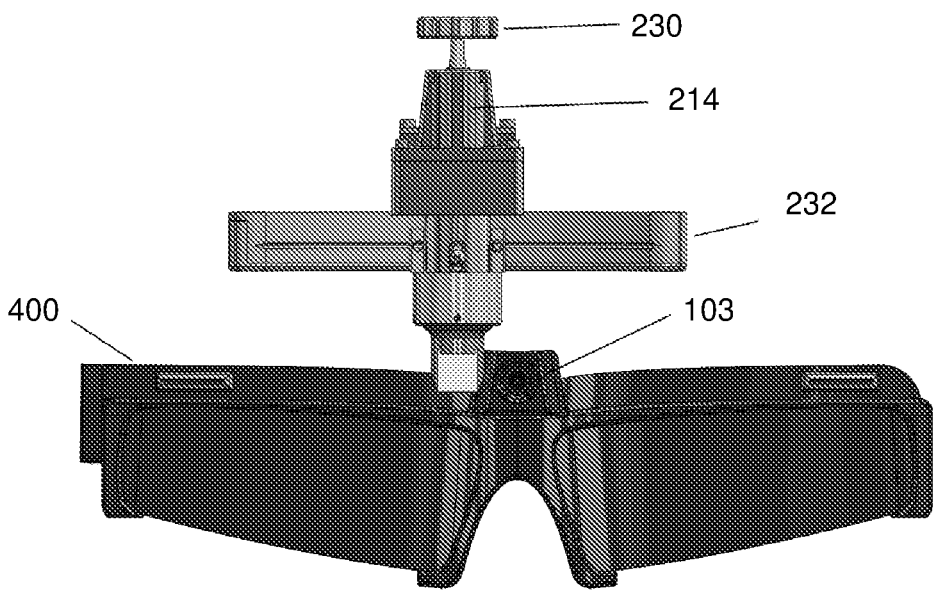
FIG. 4b illustrates a front view of an example smart glass for slit lamp imaging and ophthalmic imaging, in accordance with an embodiment of the present subject matter.

FIG. 4b illustrates a front view of an example smart glass for slit lamp imaging and ophthalmic imaging, in accordance with an embodiment of the present subject matter. As shown in the FIG. 4b, the slit width changing knob 230 is used for changing the width of the light source of the illumination assembly 214. Further, the illumination assembly 214 is provided on the slit angle changing assembly 232 for changing the angle of illumination assembly 214 by 45 degrees on both the sides of the imaging axis of the imaging lens (not shown in fig).

Figure 4C:
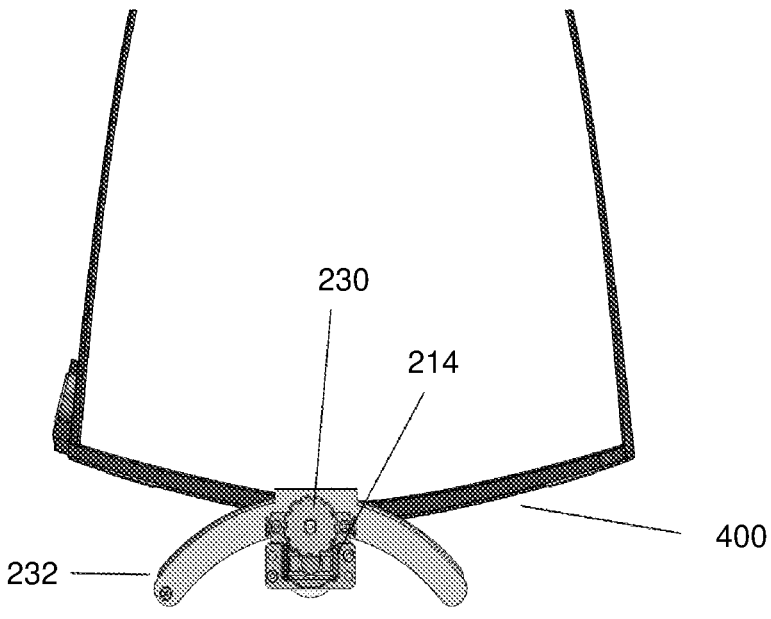
FIG. 4c illustrates a top view of an example smart glass for slit lamp imaging and ophthalmic imaging, in accordance with an embodiment of the present subject matter.
Figure 4D:
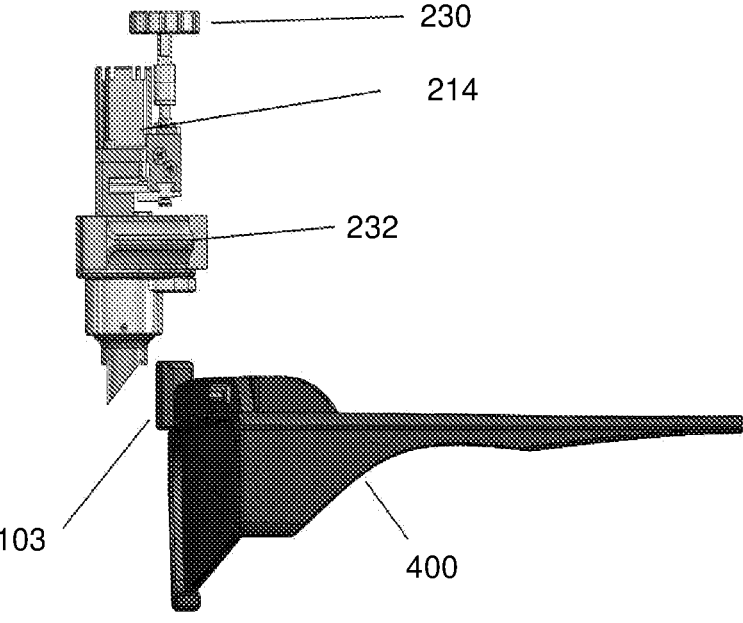
FIG. 4d illustrates a side view of an example smart glass for slit lamp imaging and ophthalmic imaging, in accordance with an embodiment of the present subject matter.

FIG. 4c illustrates a top view of an example smart glass for slit lamp imaging and ophthalmic imaging, and FIG. 4d illustrates a side view of an example smart glass for slit lamp imaging and ophthalmic imaging, in accordance with an embodiment of the present subject matter.

Figure 4E:
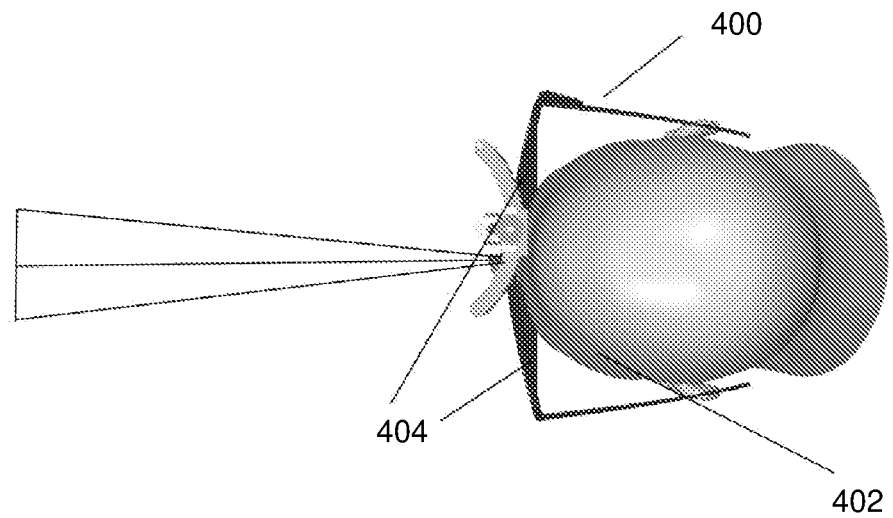
FIG. 4e illustrates a top view of an example smart glass worn by an ophthalmologist for slit lamp imaging and ophthalmic imaging, in accordance with an embodiment of the present subject matter.

FIG. 4e illustrates a top view of an example smart glass 400 worn by an ophthalmologist 402 for slit lamp imaging and ophthalmic imaging, in accordance with an embodiment of the present subject matter. The smart glass 400 is used as the 3D viewing unit 102 for imaging the 3D images or videos of various structures of the eye. In an example, one or more imaging lenses (not shown in Fig) may be placed in front of a camera of smart glass for both ophthalmic imaging and slit lamp imaging. In an example, when utilized with the camera included in the smart glass 400, the one or more imaging lenses may provide a magnification of about 0.5× to 0.8×. In the example, the magnification of 0.5× to 0.8× may be achieved by utilizing the digital zoom of the camera of the smartphone. Further, the magnification may be switched to either 2× or 4× by changing a combination of the one or more imaging lenses 106 being utilized with the camera of the smart glass. The magnification of 2× and/or 4× may also be achieved by changing the combination of the one or more imaging lenses along with utilization of the digital zoom of the camera of the smart glass.

As has been discussed, the captured 2D images or 2D videos are converted into 3D images or 3D videos using the processor 114 of the eye imaging unit 104 which is then displayed on the two displays 404 of the smart glass 400. In an example, the 2D image is split into two screens to project on displays 404 with a bit of path difference thus, a 3D image will be displayed on two displays 404 of smart glass 400.

The 3-dimensional imaging device can also be used for various applications such as indirect/direct ophthalmoscope imaging/video, Gonioscope imaging, laser surgery imaging, Retinopathy of prematurity imaging, Anterior segment imaging, Narrow and wide-angle imaging, fundus fluorescein angiography, etc. In one example, when the 3-dimensional imaging device is used for gonioscope imaging, a gonio lens may be placed between the smart glass and the eye. Thus, the 3-dimensional imaging device of the present subject matter allows an ophthalmologist to view images or videos of eye for various applications in 3-dimensions and to automatically capture the 3D images in real time.

Figure 5:
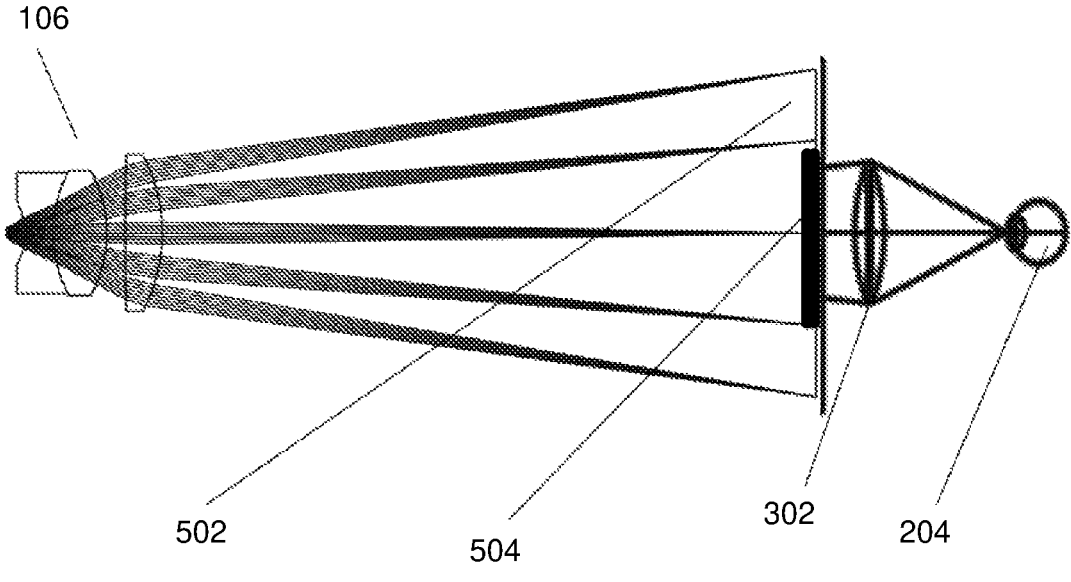
FIG. 5 illustrates an optical layout for wide and narrow angle imaging, in accordance with an embodiment of the present subject matter.

FIG. 5 illustrates an optical layout for wide and narrow angle imaging, in accordance with an embodiment of the present subject matter. In an example, the imaging lens 106 of wide angle and narrow angle are used for capturing wide angle 502 and narrow angle 504 view of the eye. Further, the condensing lens 302 may be placed in between the imaging lens 106 and the eye 204 of the patient. In an example, the wide angle and the narrow angle may be captured using both smart glass and VR box.

Figure 6A:
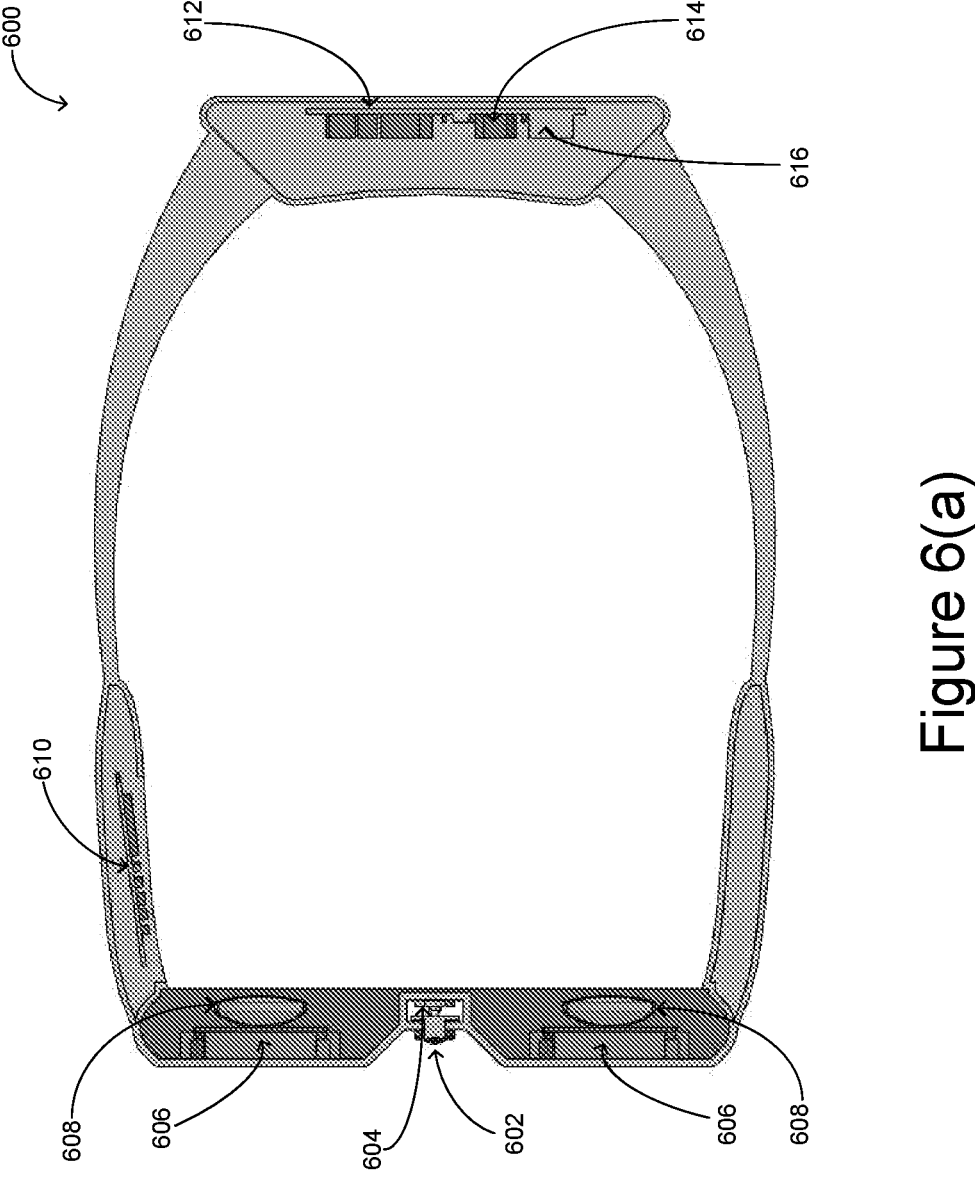
FIG. 6(a) illustrates a top perspective view of a binocular ophthalmoscope based on Liquid Crystal on Silicon (LCOS) technology as the 3D viewing unit, in accordance with an example of the present subject matter.

In an example implementation, a binocular ophthalmoscope 600 based on the Liquid Crystal on Silicon (LCOS) technology may be used as the 3D viewing unit 102 for imaging the 3D images or videos of various structures of the eye. FIG. 6(a) illustrates a top perspective view of such a binocular ophthalmoscope 600, in accordance with an example of the present subject matter.

The binocular ophthalmoscope 600 may include a camera module 602 to view and capture pictures of the structures of the eye. The camera module 602 may be embedded on a front portion of the binocular ophthalmoscope 600, in an example. The binocular ophthalmoscope 600 may further include an LED module 604 coupled to the camera module 602, where the LED module 604 may illuminate the structures of the eye whose images are to be captured. In an example, the LED module 604 may include an infrared LED and a multicolor LED for illumination the structures of the eye. Similar to the camera module 602, the LED module 604 may also be placed on the front portion of the binocular ophthalmoscope 600, in an example.

The binocular ophthalmoscope 600 may further include two LCOS displays 606 for displaying the images and/or videos of the structures of the eye captured by the camera module 602. In an example, each of the LCOS displays 606 may be coupled to a compensation lens 608, where the compensation lens 608 may be used for correcting refractive power of an eye of a user wearing the binocular ophthalmoscope 600.

The binocular ophthalmoscope 600 may further include a LCOS driver board 610 for controlling the operations of the camera module 602, the LED module 604 coupled to the camera module 602, and each of the LCOS displays 606. In operation, the LCOS driver board 606 may cause the LED module 604 to illuminate the structures of the eye. The LCOS driver board 610 may then cause the camera module 602 to capture images and/or videos of the structures of the eye. In an example, the camera module 602 may capture 2D images and/or videos of the structures of the eye. While the camera module 602 captures the 2D images and/or videos of the structures of the eye, an imaging lens (not shown) may be kept and/or held between the camera module 602 and the eye. In an example, when utilized with the camera included in the binocular ophthalmoscope 600, the one or more imaging lenses may provide a magnification of about 0.5× to 0.8×. In the example, the magnification of 0.5× to 0.8× may be achieved by utilizing the digital zoom of the camera of the binocular ophthalmoscope 600. Further, the magnification may be switched to either 2× or 4× by changing a combination of the one or more imaging lenses 106 being utilized with the camera of the binocular ophthalmoscope 600. The magnification of 2× and/or 4× may also be achieved by changing the combination of the one or more imaging lenses along with utilization of the digital zoom of the camera of the binocular ophthalmoscope 600.

In an example, the binocular ophthalmoscope 600 may also include multiple knobs (not shown), such as a magnification switching knob for changing the magnification of the structures of the eye. In the example, the magnification may be changed by controlling magnification of the camera module.

In the example, the 2D images and/or videos may then be sent to a computing unit 612 of the binocular ophthalmoscope. The computing unit 612 may be implemented as microprocessors, microcomputers, microcontrollers, digital signal processors, central processing units, state machines, logic circuitries, and/or any devices that manipulate signals based on operational instructions. Among other capabilities, the computing unit 612 may fetch and execute computer-readable instructions. The functions of the computing unit may be provided through the use of dedicated hardware as well as hardware capable of executing machine readable instructions.

The computing unit 612 may convert the 2D images and/or videos into 3D images and/or videos and transmit the same to be rendered on each of the LCOS displays 606. The 2D images and/or videos may be converted into 3D images and/or videos through techniques known in the state of the art. Accordingly, details related to the conversion of the 2D images and/or videos into 3D images and/or videos has not been included here for the sake of brevity. It would be noted that while the binocular ophthalmoscope 600 has been described to include the LCOS displays 606 for rendering the 3D images and/or videos of the structure of the eye, the binocular ophthalmoscope 600 may also include other displays, such as high definition (HD) miniature displays for rendering the 3D images and/or videos of the structure of the eye.

The binocular ophthalmoscope 600 may further include a LED driver 614 for controlling the operation of the LED module 604. In an example, the LED driver may be utilized for controlling brightness of the LED module and switching between different colors of the multicolor LED. The multicolor LED may have wavelength and functionality as that of traditional color filters that are used for viewing various structures of the eye. In an example, the different colors of the multicolor LED may be switched to view and capture different structures of the eye. For instance, when images and/or videos of nerves present within retina of the eye are to be captured, the LCOS driver board 610 may switch the multicolor LED to emit red light. It would be noted that to capture the images and/or videos of the structures of the eye, the infrared LED and the multicolor LED may be illuminated simultaneously. In an example, the LED module 604 may further be moved by 45 degrees on both the sides of the imaging axis of the imaging lens (not shown in fig).

A battery 616 may further be included in the binocular ophthalmoscope 600, where the battery 616 may be utilized for supplying power to various components included in the binocular ophthalmoscope 600.

In an example, the binocular ophthalmoscope 600 may further include one or more gesture recognition sensors (not shown). The gesture recognition sensors may identify one or more gestures and may accordingly control operation of the imaging device. In an example, the gesture recognition sensor may be coupled to the machine learning module 110, where the machine learning module 110 may utilize a machine learning model to detect the gestures and identify a corresponding operation to be performed on the imaging device. In the example, the machine learning model may be trained based on multiple gestures and operations corresponding to each of the multiple gestures.

In another example, the binocular ophthalmoscope 600 may also include other sensors, such as a microphone, to receive audio commands. In the example, the other sensors may be coupled to the machine learning module where the machine learning module may utilize a machine learning model to detect the audio commands and identify a corresponding operation to be performed on the imaging device. In the example, the machine learning model may be trained based on multiple audio commands and operations corresponding to each of the multiple audio commands.

Figure 6B:
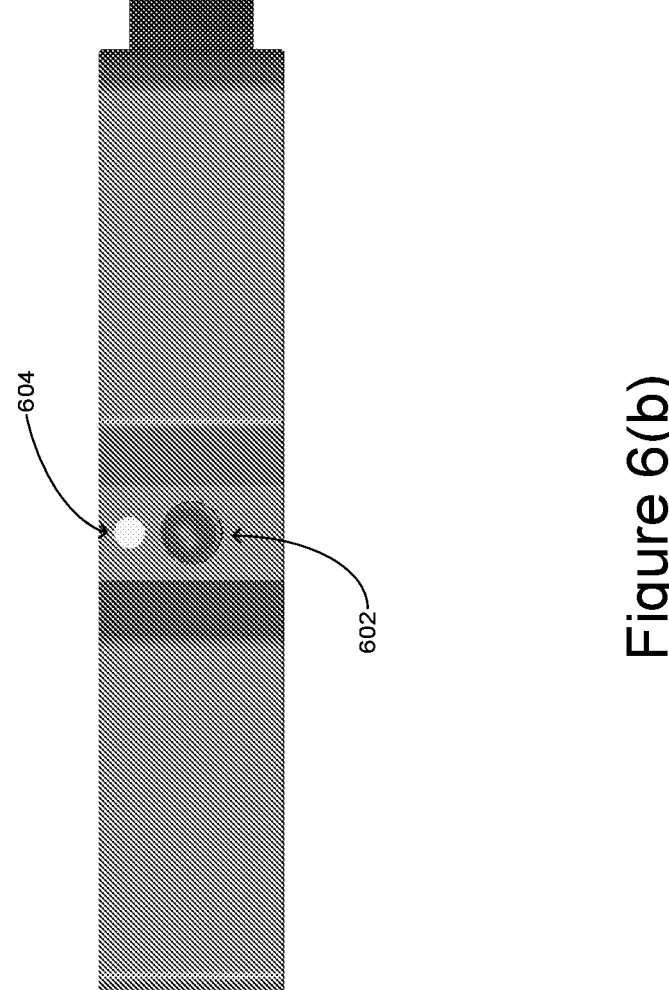
FIG. 6(b) illustrates a front perspective view of a binocular ophthalmoscope based on Liquid Crystal on Silicon (LCOS) technology as the 3D viewing unit, in accordance with an example of the present subject matter

FIG. 6(*b*) illustrates a front perspective view of the binocular ophthalmoscope 600 based on the LCOS technology, in accordance with an example of the present subject matter. As illustrated, the binocular ophthalmoscope 600 may include the camera module 602 and LED module 604 at the front portion of the binocular ophthalmoscope. The binocular ophthalmoscope 600 may further include a beam shaping optics 618 for redistributing the irradiance and phase of a light emitted by the LED module.

The 3-dimensional imaging device can also be used for various applications such as indirect/direct ophthalmoscope imaging/video, Gonioscope imaging, laser surgery imaging, Retinopathy of prematurity imaging, Anterior segment imaging, Narrow and wide-angle imaging, fundus fluorescein angiography, etc. In one example, when the 3-dimensional imaging device is used for gonioscope imaging, a gonio lens may be placed between the binocular ophthalmoscope and the eye. Thus, the 3-dimensional imaging device of the present subject matter allows an ophthalmologist to view images or videos of eye for various applications in 3-dimensions and to automatically capture the 3D images in real time.

Although the subject matter has been described in considerable detail with reference to certain examples and implementations thereof, other implementations are possible. As such, the scope of the present subject matter should not be limited to the description of the preferred examples and implementations contained therein.

We claim:

1. An imaging device for imaging structures of an eye, the imaging device comprising:

an eye imaging unit to capture images of the structures of the eye, the eye imaging unit comprising:

a control module;

an illumination module coupled to the control module, to illuminate the structures of the eye, wherein the illumination module illuminates the structures of the eye with infrared light, wherein the illumination module is moveable along an axis perpendicular to an imaging axis of the imaging lens by 45 degrees on both sides of the imaging axis; and an imaging lens coupled to the control module and the illumination module to view and magnify the structures of the eye, wherein the imaging lens provides multiple magnifications of the structures of the eye;

an imaging module coupled to the eye imaging unit to capture 2D images of the structures of the eye; and a 3D viewing unit coupled to the imaging module, wherein the 3D viewing unit is to convert the 2D images to 3D images, wherein the control module is to control movement of the illumination module by 45 degrees on both sides of the imaging axis of the imaging lens.

2. The imaging device as claimed in claim 1, wherein the control module is to control the movement of the illumination module to a position off the imaging axis of the imaging lens.

3. The imaging device as claimed in claim 1, wherein the illumination module further comprises an illumination assembly, wherein the illumination assembly comprises an infrared light emitting diodes (LED) and a multicolor LED for illuminating the structures of the eye.

4. The imaging device as claimed in claim 3, wherein the illumination module further comprises a light intensity control knob to control an intensity of light emitted by the multicolor LEDs.

5. The imaging device as claimed in claim 3, wherein the illumination module further comprises an illumination circle diameter changing knob to change a size of an illumination circle being formed by the infrared LED.

6. The imaging device as claimed in claim 5, wherein the 3D viewing unit comprises a smartphone, and wherein the imaging module is a camera included in the smartphone.

7. The imaging device as claimed in claim 6, wherein the imaging lens is to utilize digital zoom of the camera included in the smartphone to provide multiple magnifications of the structures of the eye.

8. The imaging device as claimed in claim 6, wherein the 3D viewing unit is to utilize an application installed on the smartphone to convert the 2D images to 3D images.

9. The imaging device as claimed in claim 1, wherein the 3D viewing unit is one of a virtual reality (VR) box, a smart glass, and a binocular ophthalmoscope based on the Liquid Crystal on Silicon (LCOS) technology.

10. The imaging device as claimed in claim 1, wherein the 3D viewing unit further comprises a plurality of gesture recognition sensors to detect one or more gestures to perform an operation on the imaging device.

11. The imaging device as claimed in claim 10, further comprising a machine learning module coupled to the plurality of gesture recognition sensors, wherein the machine learning module is to utilize a machine learning model trained based on a plurality of gestures and operations corresponding to each of the plurality of gestures, to identify an operation to be performed on the imaging device.

12. The imaging device as claimed in claim 1, further comprising a microphone to detect audio commands to perform an operation on the imaging device.

13. The imaging device as claimed in claim 12, further comprising a machine learning module coupled to the microphone, wherein the machine learning module is to utilize a machine learning model trained based on a plurality of audio commands and operations corresponding to each of the plurality of audio commands, to identify an operation to be performed on the imaging device.

14. The imaging device as claimed in claim 1, wherein the imaging module is to capture the 2D images of the structures of the eye without dilation of the eye.

* * * * *